US008263766B2

(12) United States Patent
Tsuchida

(10) Patent No.: US 8,263,766 B2
(45) Date of Patent: Sep. 11, 2012

(54) MELAMINE-FUNCTIONAL ORGANOSILICON COMPOUND AND MAKING METHOD

(75) Inventor: Kazuhiro Tsuchida, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 170 days.

(21) Appl. No.: 12/827,664

(22) Filed: Jun. 30, 2010

(65) Prior Publication Data

US 2011/0003989 A1    Jan. 6, 2011

(30) Foreign Application Priority Data

Jul. 1, 2009   (JP) ................................. 2009-156463

(51) Int. Cl.
*C07D 251/70* (2006.01)
(52) U.S. Cl. ......... 544/196; 544/200; 544/201; 544/203
(58) Field of Classification Search .................. 544/201, 544/203, 196, 200
See application file for complete search history.

(56) References Cited

U.S. PATENT DOCUMENTS

| 2,949,434 | A | 8/1960 | Bailey et al. |
| 6,517,742 | B1 | 2/2003 | Richard et al. |
| 2005/0008588 | A1 | 1/2005 | Candau et al. |
| 2010/0003207 | A1 | 1/2010 | Candau et al. |

FOREIGN PATENT DOCUMENTS

| CN | 101433826 A | 5/2009 |
| EP | 0103986 A2 | 3/1984 |
| EP | 0841341 A1 | 5/1998 |
| EP | 1484051 A2 | 12/2004 |
| EP | 1927343 A1 | 6/2008 |
| JP | 7-26242 A | 1/1995 |
| JP | 11-100237 A | 4/1999 |
| JP | 2001-158166 A | 6/2001 |
| JP | 2001-158167 A | 6/2001 |
| JP | 2006-213677 A | 8/2006 |
| JP | 2007-131556 A | 5/2007 |
| WO | WO 2009/074409 A1 | 6/2009 |

OTHER PUBLICATIONS

Arrachart, Guilhem et al., "Silylated Melamine and Cyanuric Acid as Precursors for Imprinted and Hybrid Silica Materials with Molecular Recognition Properties," Chemistry A European Journal, vol. 15, pp. 6279-6288, XP002602872, May 13, 2009.
Braun, Von Dietrich et al., "Strukturaufklärung der Methylolmelamine," Die Angewandte Makromolekulare, vol. 34, No. 499, pp. 35-53, XP009138917, Jan. 1, 1973.
Campbell, J. Robert et al., "Unsymmetrically Substituted Melamines," Journal of Organic Chemistry, vol. 26, No. 8, pp. 2786-2789, XP002602873, Aug. 1961.
European Search Report dated Oct. 14, 2010 for Application No. 10251186.2.
Goan, J. C. et al., "Silicon-Containing s-Triazine Derivatives," Journal of Organic Chemistry, vol. 27, pp. 2657-2658, XP001005354, Jul. 7, 1962.
Karies, Stefan et al., "Novel Precursors for Inorganic-Organic Hybrid Materials," Organosilicon Chemistry III: From Molecules to Materials, Wiley-VCH, pp. 543-549, XP009139113, Jan. 1, 1998.
Yoo, Sukjoon et al., "Reverse-selective membranes formed by dendrimers on mesoporous ceramic supports," Journal of Membrane Science, vol. 334, Nos. 1-2, pp. 16-22, XP026035728, May 15, 2009.
Kapoor et al., "Catalysts by Mesoporous Dendrimers," Topics in Catalysts (2009), vol. 52, pp. 634-642.
Office Action issued Nov. 9, 2011, in Japanese Patent Application No. 2009-156463.

*Primary Examiner* — Venkataraman Balasubramanian
(74) *Attorney, Agent, or Firm* — Birch, Stewart, Kolasch & Birch, LLP

(57) ABSTRACT

A melamine skeleton-bearing organosilicon compound has a film forming ability, water solubility and compatibility with resins. It is prepared by reacting cyanuric chloride with a primary and/or secondary amine compound and neutralizing with a base.

4 Claims, 3 Drawing Sheets

MELAMINE-FUNCTIONAL ORGANOSILICON COMPOUND AND MAKING METHOD

CROSS-REFERENCE TO RELATED APPLICATION

This non-provisional application claims priority under 35 U.S.C. §119(a) on Patent Application No. 2009-156463 filed in Japan on Jul. 1, 2009, the entire contents of which are hereby incorporated by reference.

TECHNICAL FIELD

This invention relates to a melamine-functional organosilicon compound and a method for preparing the same. More particularly, it relates to a multi-functional silyl compound having a melamine skeleton in the molecule which has high water solubility and is able to form a film upon hydrolytic condensation because of the melamine skeleton combined with the siloxane structure.

BACKGROUND ART

One typical group of organosilicon compounds is silane coupling agents. The silane coupling agents have two or more different functional radicals in their molecule, and serve as a chemical bridge to bond an organic material and an inorganic material that would otherwise be difficult to bond. In the silane coupling agent, one functional radical is a hydrolyzable silyl radical which forms a silanol radical in the presence of water. This silanol radical, in turn, reacts with a hydroxyl radical on the surface of inorganic material to form a chemical bond to the inorganic material surface. The other functional radicals include vinyl, epoxy, amino, (meth)acrylic, mercapto and similar radicals which form a chemical bond with organic materials such as various synthetic resins, as well as ureido, isocyanurate and other polar radicals which do not form a chemical bond, but hydrogen bond or otherwise interact due to their polarity. By virtue of these attributes, the silane coupling agents are widely used as modifiers, adhesive aids, and various other additives in organic and inorganic resins.

Among others, those silane coupling agents having non-bonding functional radicals such as ureido and isocyanurate are used as resin modifiers and paint additives. Generally isocyanurate silane coupling agents are advantageous in that their hydrolytic condensates have a film forming ability since they are of tris(silyl) type, and that they are compatible with resins because of inclusion of polar radicals. However, these silane coupling agents find limited use in aqueous applications because of a lack of water solubility.

Heterocyclic structures similar to isocyanurate include triazine structures. Mono(silyl) silane coupling agents having triazine structure are disclosed in JP-A 2006-213677 and JP-A 2007-131556. These patent documents relate to only organosilicon compounds of triazine structure having a thiol radical(s) introduced therein. With such teaching, a melamine skeleton as disclosed herein cannot be formed. On account of the thiol radical being introduced, a tris(silyl) structure as disclosed herein cannot be formed.

JP-A H07-026242 discloses an adhesive composition comprising a silicone-modified melamine resin. Since a melamine resin derivative is tied with silicone by condensation of hydroxyl with silanol, undesirably the modified resin is prone to untying in the presence of water or alcohol. Silane coupling agents are nowhere described. JP-A H11-100237 discloses a composition for use as a glass fiber sizing agent, comprising a melamine resin and a reactive silane coupling agent. Since this material is a blend of components, it is impossible to isolate the material as a compound and identify the structure thereof.

CITATION LIST

Patent Document 1: JP-A 2006-213677
Patent Document 2: JP-A 2007-131556
Patent Document 3: JP-A H07-026242
Patent Document 4: JP-A H11-100237

SUMMARY OF INVENTION

An object of the invention is to provide an organosilicon compound of triazine structure, specifically melamine structure, having a film forming ability, water solubility and compatibility with resins, and a method for preparing the organosilicon compound.

The inventor has found that an organosilicon compound having the desired properties is obtainable from reaction of cyanuric chloride with a primary and/or secondary amino-containing organosilicon compound having the general formula (3) shown below.

In one aspect, the invention provides a melamine skeleton-bearing organosilicon compound having the general formula (1).

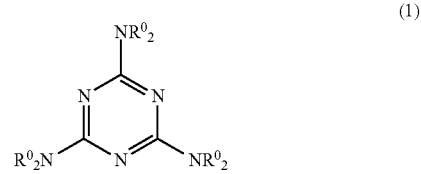

Herein $R^0$ is independently hydrogen or a substituted or unsubstituted monovalent hydrocarbon radical which may be separated by carbonyl carbon or a heteroatom selected from the group consisting of oxygen, sulfur and nitrogen, and at least one of $R^0$ is the following structure (A):

wherein the broken line designates a valence bond, X is a substituted or unsubstituted divalent hydrocarbon radical which may be separated by carbonyl carbon or a heteroatom selected from the group consisting of oxygen, sulfur and nitrogen, the divalent hydrocarbon radical bonding to the nitrogen atom via a carbon atom at one end and bonding to the silicon atom via a carbon atom at the other end, $R^1$ is independently hydrogen or a substituted or unsubstituted $C_1$-$C_4$ alkyl radical, $R^2$ is independently a substituted or unsubstituted $C_1$-$C_4$ alkyl radical, and n is an integer of 1 to 3.

In a preferred embodiment, the organosilicon compound has the general formula (2):

The organosilicon compound of the invention has a structure of the following general formula (1).

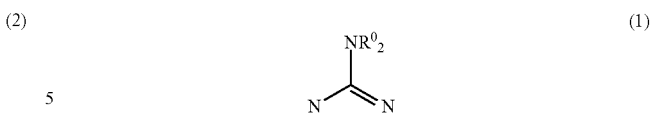

Herein $R^0$ is each independently hydrogen or a substituted or unsubstituted monovalent hydrocarbon radical which may be separated by carbonyl carbon or a heteroatom selected from the group consisting of oxygen, sulfur and nitrogen. At least one $R^0$ is the following structure (A):

wherein the broken line designates a valence bond, X is a substituted or unsubstituted divalent hydrocarbon radical which may be separated by carbonyl carbon or a heteroatom selected from the group consisting of oxygen, sulfur and nitrogen, the divalent hydrocarbon radical bonding to the nitrogen atom via a carbon atom at one end and bonding to the silicon atom via a carbon atom at the other end, $R^1$ is each independently hydrogen or a substituted or unsubstituted $C_1$-$C_4$ alkyl radical, $R^2$ is each independently a substituted or unsubstituted $C_1$-$C_4$ alkyl radical, and n is an integer of 1 to 3.

Preferably the compound has the general formula (2).

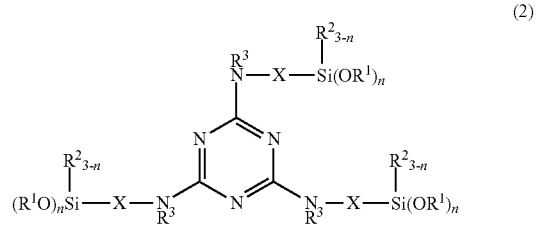

Herein X, $R^1$, $R^2$ and n are as defined above. $R^3$ is each independently hydrogen or a substituted or unsubstituted monovalent hydrocarbon radical which may be separated by carbonyl carbon or a heteroatom selected from the group consisting of oxygen, sulfur and nitrogen, preferably hydrogen or alkyl, and most preferably hydrogen.

In formulae (1) and (2), $R^0$ and $R^3$ are optionally substituted monovalent hydrocarbon radicals which may be separated by carbonyl carbon or a heteroatom selected from oxygen, sulfur and nitrogen, examples of which include alkyl radicals such as methyl, ethyl, propyl, isopropyl, butyl, isobutyl, tert-butyl, pentyl, neopentyl, hexyl, cyclohexyl, octyl, nonyl and decyl, aryl radicals such as phenyl, tolyl, xylyl and naphthyl, aralkyl radicals such as benzyl, phenylethyl and phenylpropyl, alkenyl radicals such as vinyl, allyl, propenyl, isopropenyl, butenyl, hexenyl, cyclohexenyl and octenyl, and the following.

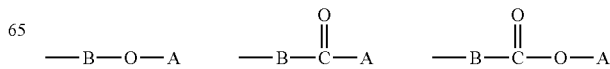

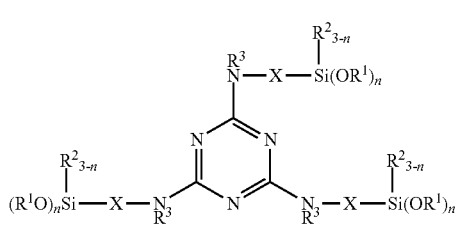

wherein X, $R^1$, $R^2$, and n are as defined above, $R^3$ is independently hydrogen or a substituted or unsubstituted monovalent hydrocarbon radical which may be separated by carbonyl carbon or a heteroatom selected from the group consisting of oxygen, sulfur and nitrogen.

In another aspect, the invention provides a method for preparing the organosilicon compound comprising the steps of reacting cyanuric chloride with a primary and/or secondary amine compound and neutralizing with a base, the primary and/or secondary amine compound comprising an organosilicon compound having the general formula (3).

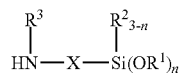

Herein X, $R^1$, $R^2$, $R^3$, and n are as defined above.

In a preferred embodiment, the reaction uses at least 4 moles of the organosilicon compound having formula (3) per mole of cyanuric chloride and occurs at a temperature of 25 to 150° C. The base is typically ethylenediamine.

ADVANTAGEOUS EFFECTS OF INVENTION

The organosilicon compound of the invention is useful as a silane coupling agent since it is fully compatible with resins due to a polar structure or melamine structure and highly water soluble due to amine functionality. It is also useful as an additive to aqueous paints since a hydrolytic condensate thereof has a film forming ability particularly when it is a multifunctional silyl melamine.

DESCRIPTION OF EMBODIMENTS

Figure 1:
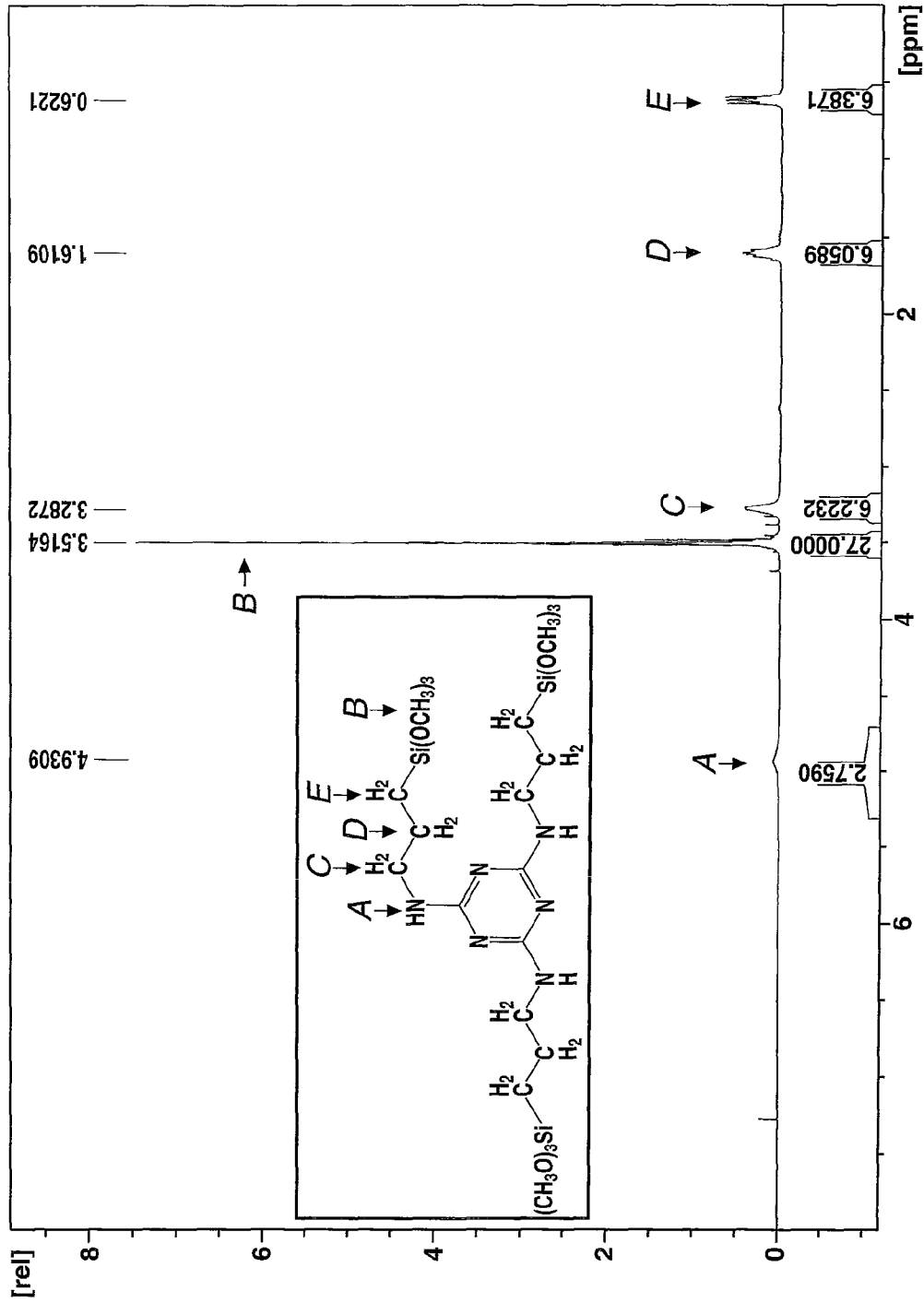
FIGS. 1, 2, and 3 show $^1$H-NMR, $^{13}$C-NMR, and $^{29}$Si-NMR spectra of the reaction product in Example 1, respectively.

The singular forms "a," "an" and "the" include plural referents unless the context clearly dictates otherwise. The notation ($C_n$-$C_m$) means a radical containing from n to m carbon atoms per radical. As used herein, the term "silane coupling agent" is encompassed by "organosilicon compound".

Organosilicon Compound

-continued

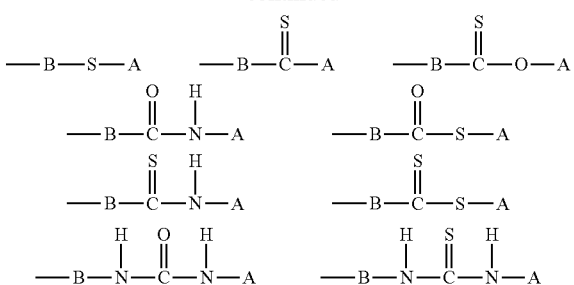

Herein A is a monovalent hydrocarbon radical, examples of which include alkyl radicals such as methyl, ethyl, propyl, isopropyl, butyl, isobutyl, and tert-butyl. B is a divalent hydrocarbon radical, examples of which include alkylene radicals such as methylene, ethylene and propylene.

It is to be noted that the substituent on the foregoing structures is a radical selected from the group consisting of alkyl, aryl, perfluoroalkyl, polyether, perfluoropolyether and hydrolyzable silyl radicals. Of these, alkyl and aryl radicals are preferred. The substituent may be attached to a polysiloxane structure as mentioned above, typically silicone oil and silicone resin, or an organic polymer structure.

In formulae (1) and (2), $R^1$ and $R^2$ are optionally substituted $C_1$-$C_4$ alkyl radicals, examples of which include methyl, ethyl, propyl, isopropyl, n-butyl, isobutyl, tert-butyl, and substituted forms of the foregoing radicals in which some or all hydrogen atoms are substituted by halogen atoms, such as chloromethyl and 3,3,3-trifluoropropyl. Preferably $R^1$ and $R^2$ each are methyl or ethyl.

In formulae (1) and (2), X is an optionally substituted divalent hydrocarbon radical which may be separated by carbonyl carbon or a heteroatom selected from oxygen, sulfur and nitrogen, the divalent hydrocarbon radical bonding to the nitrogen atom via a carbon atom at one end and bonding to the silicon atom via a carbon atom at the other end. Examples of the divalent hydrocarbon radical include, but are not limited to, methylene, ethylene, propylene, 1-methylpropylene, 2-methylpropylene, 3-methylpropylene and butylene. The subscript n is an integer of 1 to 3, preferably 2 or 3, and most preferably 3.

Examples of the melamine-functional organosilicon compound include those of structural formulae (4) to (7) below. Herein Me stands for methyl and Et for ethyl.

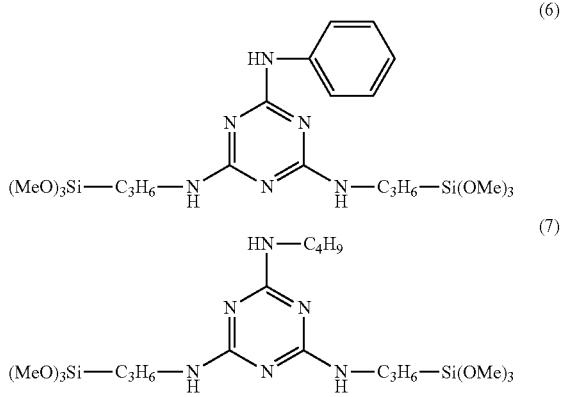

Method

The organosilicon compound of the invention may be prepared by reacting cyanuric chloride with a primary and/or secondary amine compound and neutralizing the reaction product with a base. The primary and/or secondary amine compound used herein contains, as an essential component, an organosilicon compound having both a primary and/or secondary amino radical and a hydrolyzable silyl radical, represented by the following general formula (3):

$$\underset{HN}{R^3} - X - \underset{Si(OR^1)_n}{R^2_{3-n}} \quad (3)$$

wherein X, $R^1$, $R^2$, $R^3$ and n are as defined above. To distinguish the organosilicon compound of the invention and the starting organosilicon compound containing a primary and/or secondary amino radical and a hydrolyzable silyl radical, the former is referred to as the target organosilicon compound and the latter is referred to as the organosilicon reactant, hereinafter.

The essential reactants used in the reaction are cyanuric chloride and an organosilicon reactant having both a primary and/or secondary amino radical and a hydrolyzable silyl radical. Besides, reactants having a primary and/or secondary amino radical such as hydrocarbons having a primary and/or secondary amino radical and polysiloxanes having a primary and/or secondary amino radical may be used along with the essential reactants, and then the target organosilicon compound having a melamine skeleton in the molecule can still be prepared.

Non-limiting examples of the primary and/or secondary amine compound include organosilicon compounds having both a primary and/or secondary amino radical and a hydrolyzable silyl radical such as α-aminomethyltrimethoxysilane, α-aminomethylmethyldimethoxysilane, α-aminomethyldimethylmethoxysilane, α-aminomethyltriethoxysilane, α-aminomethylmethyldiethoxysilane, α-aminomethyldimethylethoxysilane, γ-aminopropyltrimethoxysilane, γ-aminopropylmethyldimethoxysilane, γ-aminopropyldimethylmethoxysilane, γ-aminopropyltriethoxysilane, γ-aminopropylmethyldiethoxysilane, γ-aminopropyldimethylethoxysilane, N-(2-aminoethyl)-α-aminomethyltrimethoxysilane, N-(2-aminoethyl)-α-aminomethylmethyldimethoxysilane, N-(2-aminoethyl)-α-aminomethyldimethylmethoxysilane, N-(2-aminoethyl)-α-aminomethyltriethoxysilane, N-(2-aminoethyl)-α- aminomethylmethyldiethoxysilane, aminomethyldimethylethoxysilane, aminopropyltrimethoxysilane, aminopropylmethyldimethoxysilane, aminopropyldimethylmethoxysilane, aminopropyltriethoxysilane, aminopropylmethyldiethoxysilane, aminopropyldimethylethoxysilane, N-(2-aminoethyl)-α-aminomethyldimethylethoxysilane, N-(2-aminoethyl)-γ-aminopropyltrimethoxysilane, N-(2-aminoethyl)-γ-aminopropylmethyldimethoxysilane, N-(2-aminoethyl)-γ-aminopropyldimethylmethoxysilane, N-(2-aminoethyl)-γ-aminopropyltriethoxysilane, N-(2-aminoethyl)-γ-aminopropylmethyldiethoxysilane, N-(2-aminoethyl)-γ-aminopropyldimethylethoxysilane, bis(trimethoxysilylpropyl)amine, bis(methyldimethoxysilylpropyl)amine, bis(dimethylmethoxysilylpropyl)amine, bis(triethoxysilylpropyl)amine, bis(methyldiethoxysilylpropyl)amine, bis(dimethylethoxysilylpropyl)amine, N-phenyl-γ-aminopropyltrimethoxysilane, N-phenyl-γ-aminopropylmethyldimethoxysilane, N-phenyl-γ-aminopropyldimethylmethoxysilane, N-phenyl-γ-aminopropyltriethoxysilane, N-phenyl-γ-aminopropylmethyldiethoxysilane, N-phenyl-γ-aminopropyldimethylethoxysilane, N-phenyl-α-aminomethyltrimethoxysilane, N-phenyl-α-aminomethylmethyldimethoxysilane, N-phenyl-α-aminomethyldimethylmethoxysilane, N-phenyl-α-aminomethyltriethoxysilane, N-phenyl-α-aminomethylmethyldiethoxysilane, and N-phenyl-α-aminomethyldimethylethoxysilane; and organosilicon compounds having a primary and/or secondary amino radical such as similar alkoxysilane oligomers having a primary and/or secondary amino radical.

In the production of the target organosilicon compound, cyanuric chloride and the organosilicon reactant having both a primary and/or secondary amino radical and a hydrolyzable silyl radical may be combined at any desired ratio. It is preferred from the aspects of reactivity and productivity to use 4 to 20 moles and more preferably 4.5 to 10 moles of the organosilicon reactant per mole of cyanuric chloride. This is true particularly when a tris(trialkoxysilyl) melamine compound is to be produced. If the amount of the organosilicon reactant is too small, hydrogen chloride generated during the reaction may form a salt with an amino radical to detract from the reactivity, resulting in a decline of productivity. Besides the unreacted reactants may be entrained as impurities to reduce the purity of the tris(trialkoxysilyl) compound. Too much amounts of the organosilicon reactant may simply add to the cost of production because the reaction may be saturated.

When another reactant having a primary and/or secondary amino radical is used in the reaction with cyanuric chloride, the total amount of the organosilicon reactant having both a primary and/or secondary amino radical and a hydrolyzable silyl radical and the other reactant having a primary and/or secondary amino radical is preferably 4 to 20 moles and more preferably 4.5 to 10 moles per mole of cyanuric chloride. The organosilicon reactant is preferably blended with the other reactant in such a molar ratio as to meet 0<(other reactant)/(organosilicon reactant)≦2 and more preferably 0.5≦(other reactant)/(organosilicon reactant)≦2.

A solvent may be used in the production of the target organosilicon compound, if desired. The solvent used is not particularly limited as long as it is nonreactive with the reactants, cyanuric chloride and primary and/or secondary amine compounds. Examples include aliphatic hydrocarbon solvents such as pentane, hexane, heptane and decane, ether solvents such as diethyl ether, tetrahydrofuran and 1,4-dioxane, and aromatic hydrocarbon solvents such as benzene, toluene and xylene.

The reaction to produce the target organosilicon compound is exothermic. Since side reactions can occur at unnecessarily high temperatures, the reaction temperature is preferably controlled in a range of 25° C. to 150° C., more preferably 35° C. to 120° C., and most preferably 50° C. to 120° C. Below 25° C., the reaction rate may be retarded to invite a decline of productivity and side reactions may concomitantly occur to reduce the purity. A temperature of higher than 150° C. may cause pyrolysis, leading to a low purity.

The reaction time required to produce the target organosilicon compound is not particularly limited as long as the above-mentioned temperature management during exothermic reaction is possible and the exothermic reaction is brought to completion. The reaction time is preferably about 10 minutes to about 24 hours and more preferably about 1 hour to about 20 hours.

The method for the production of the target organosilicon compound should involve a neutralization step after the reaction since hydrochloric acid generates during the reaction. The base used for neutralization is not particularly limited as long as it forms with hydrogen chloride a salt in insoluble solid or liquid form which can be separated. Suitable bases include trialkylamines, ethylenediamine, urea, metal alkoxides and the like. Of these, ethylenediamine is preferred because it effectively forms a hydrochloride salt in liquid form which can be readily separated.

In the production of the target organosilicon compound, the amount of the base added for neutralization is 1 to 3 moles, and preferably 1.2 to 2 moles per mole of hydrogen chloride generated on a stoichiometric basis. If the amount of the base added is too small, only a fraction of hydrochloric acid may be trapped, resulting in the target compound having an increased chloride ion content. Too much amounts of the base may simply add to the cost of production because the neutralization reaction is saturated.

The temperature of the neutralization step is preferably controlled in a range of 25° C. to 150° C., more preferably 35° C. to 120° C., and most preferably 50° C. to 120° C. Below 25° C., the reaction rate may be retarded, resulting in a decline of productivity. A temperature of higher than 150° C. may cause pyrolysis, leading to a low purity. The neutralization time is preferably about 10 minutes to about 24 hours and more preferably about 1 hour to about 20 hours.

EXAMPLE

Examples of the invention are given below by way of illustration and not by way of limitation. In Examples, the viscosity is measured at 25° C. by a capillary viscometer. The specific gravity and refractive index are also measured at 25° C. Nuclear magnetic resonance spectroscopy is abbreviated as NMR. Me stands for methyl and Et for ethyl.

Example 1

Preparation of N,N,N-tris(trimethoxysilylpropyl)melamine

Figure 2:
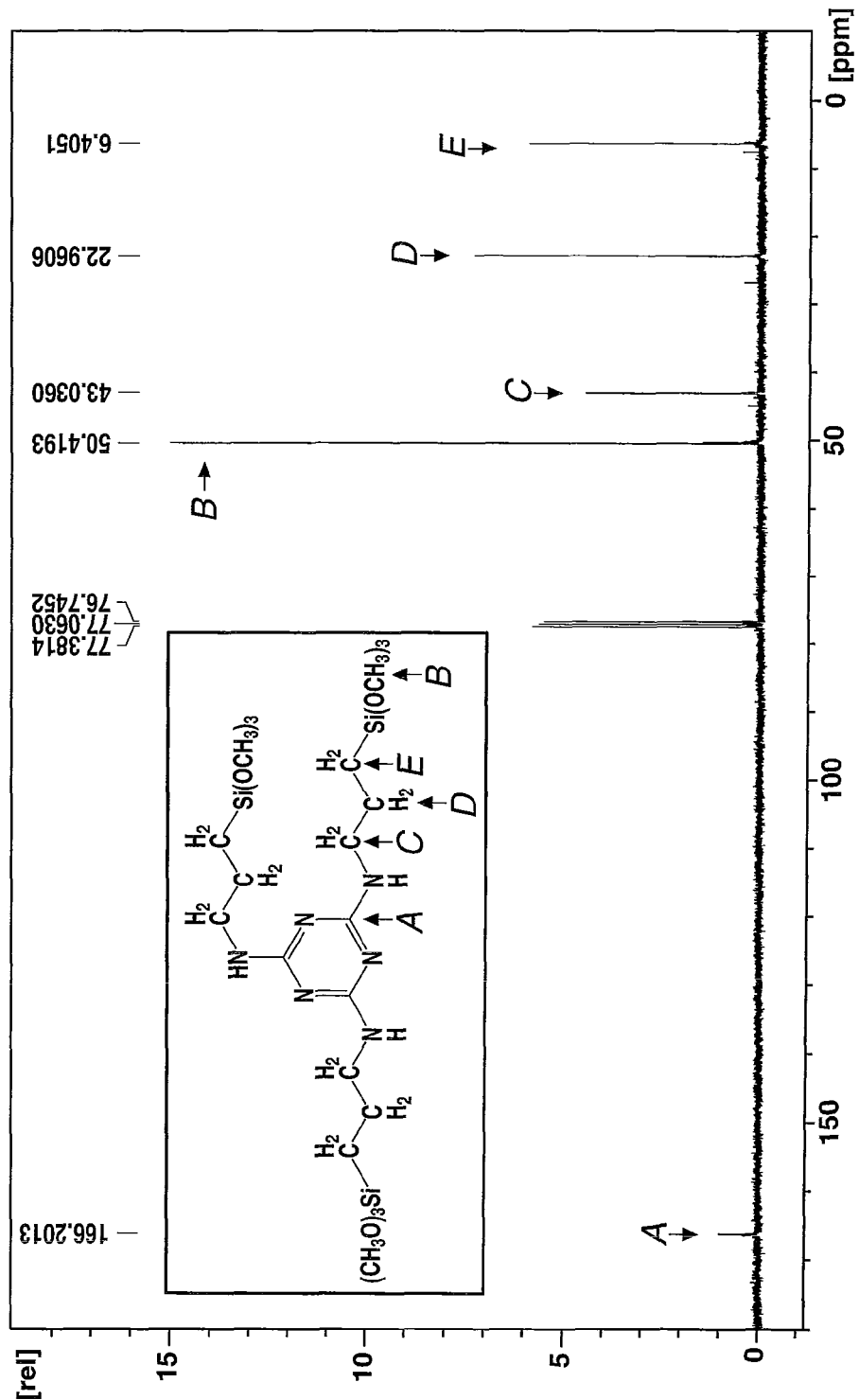
Figure 3:
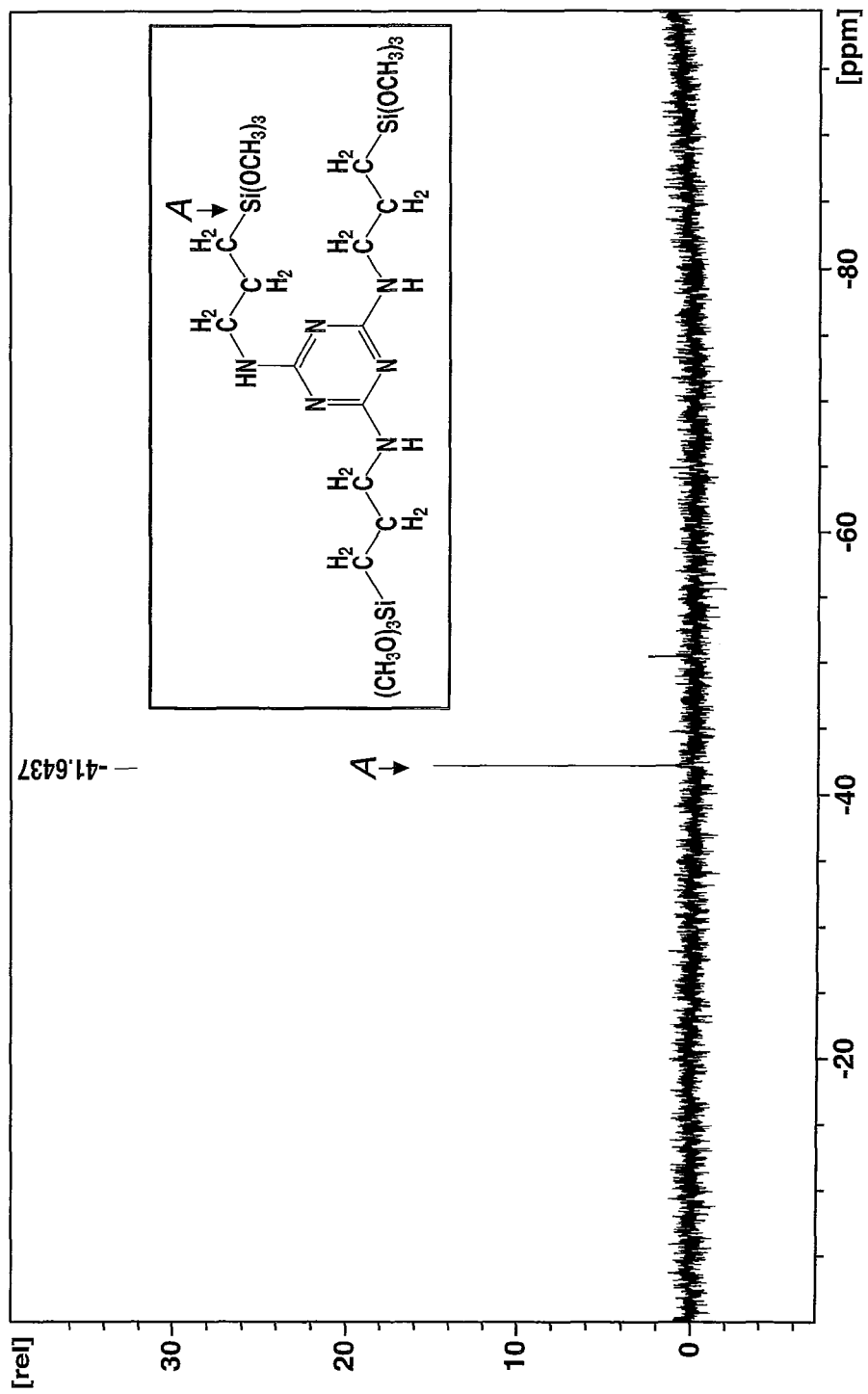

A 1-L separable flask equipped with a stirrer, reflux condenser, dropping funnel and thermometer was charged with 55.3 g (0.3 mol) of cyanuric chloride and 300 g of toluene, which were stirred while heating to an internal temperature of 50° C. To the flask 403.3 g (2.2 mol) of γ-aminopropyltrimethoxysilane (KBM-903, Shin-Etsu Chemical Co., Ltd.) was added dropwise. The reaction was exothermic and the internal temperature rose to 80° C. Stirring was continued for 8 hours while heating to an internal temperature of 110° C. After the reaction, the temperature was adjusted to 80° C. To the flask 81 g (1.3 mol) of ethylenediamine was added dropwise for neutralization over 4 hours. The reaction solution separated into two layers. The upper layer was taken out, from which the solvent and unreacted substances were distilled off under vacuum. The reaction product was left as a pale yellow liquid having a viscosity of 1,690 mm²/s, a specific gravity of 1.15 and a refractive index of 1.489. On NMR spectroscopy, the reaction product was identified to be a single compound having the following chemical structural formula (4). FIGS. 1, 2 and 3 show ¹H-NMR, ¹³C-NMR and ²⁹Si-NMR spectra of the compound, respectively.

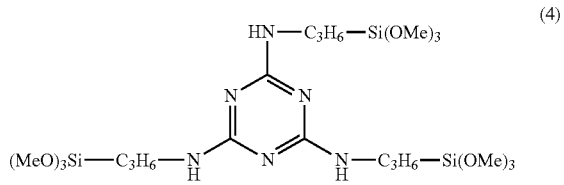

(4)

Example 2

Preparation of N,N,N-tris(triethoxysilylpropyl)melamine

A 1-L separable flask equipped with a stirrer, reflux condenser, dropping funnel and thermometer was charged with 55.3 g (0.3 mol) of cyanuric chloride and 300 g of toluene, which were stirred while heating to an internal temperature of 50° C. To the flask 486.9 g (2.2 mol) of γ-aminopropyltriethoxysilane (KBE-903, Shin-Etsu Chemical Co., Ltd.) was added dropwise. The reaction was exothermic and the internal temperature rose to 80° C. Stirring was continued for 8 hours while heating to an internal temperature of 110° C. After the reaction, the temperature was adjusted to 80° C. To the flask 81 g (1.3 mol) of ethylenediamine was added dropwise for neutralization over 4 hours. The reaction solution separated into two layers. The upper layer was taken out, from which the solvent and unreacted substances were distilled off under vacuum. The reaction product was left as a pale yellow liquid having a viscosity of 1,730 mm²/s, a specific gravity of 1.08 and a refractive index of 1.485. On NMR spectroscopy, the reaction product was identified to be a single compound having the following chemical structural formula (5). NMR spectroscopy data of the compound are shown below.

¹H-NMR (300 MHz, CDCl₃, δ (ppm)): 0.58 (t, 6H), 0.82 (t, 27H), 1.63 (quint, 6H), 3.30 (t, 6H), 3.45 (q, 18H), 4.88 (s, 3H)

¹³C-NMR (75 MHz, CDCl₃, δ (ppm)): 6.2, 18.1, 23.3, 43.5, 50.9, 166.8

²⁹Si-NMR (60 MHz, CDCl₃, δ (ppm)): −41.8

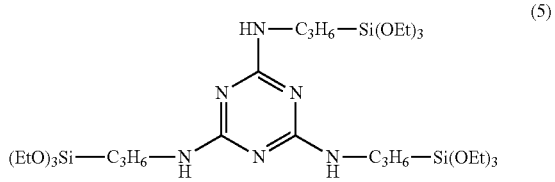

(5)

Example 3

Preparation of N,N-bis(trimethoxysilylpropyl)-N-phenyl-melamine

A 1-L separable flask equipped with a stirrer, reflux condenser, dropping funnel and thermometer was charged with 55.3 g (0.3 mol) of cyanuric chloride and 300 g of toluene, which were stirred while heating to an internal temperature of 50° C. To the flask a mixture of 179.3 g (1.4 mol) of γ-aminopropyltrimethoxysilane (KBM-903, Shin-Etsu Chemical Co., Ltd.) and 65.1 g (0.7 mol) of aniline was added dropwise. The reaction was exothermic and the internal temperature rose to 80° C. Stirring was continued for 8 hours while heating to an internal temperature of 110° C. After the reaction, the temperature was adjusted to 80° C. To the flask 81 g (1.3 mol) of ethylenediamine was added dropwise for neutralization over 4 hours. The reaction solution separated into two layers. The upper layer was taken out, from which the solvent and unreacted substances were distilled off under vacuum. The reaction product was left as a pale yellow liquid having a viscosity of 2,210 mm²/s, a specific gravity of 1.05 and a refractive index of 1.493. On NMR spectroscopy, the reaction product was identified to be a compound of the following chemical structural formula (6) having alkoxysilyl and phenyl radicals in a ratio of 2:1. ¹H-NMR spectroscopy data of the compound are shown below.

¹H-NMR (300 MHz, CDCl₃, δ (ppm)): 0.61 (t, 4H), 1.69 (quint, 4H), 3.22 (t, 4H), 3.56 (s, 18H), 4.91-5.04 (s, 3H), 6.64-7.11 (m, 5H)

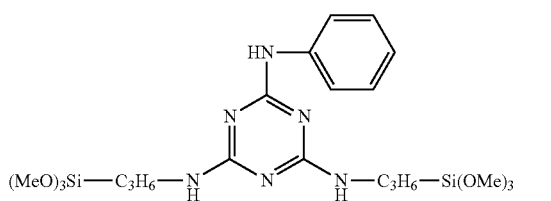

(6)

Example 4

Preparation of N,N-bis(trimethoxysilylpropyl)-N-butyl-melamine

A 1-L separable flask equipped with a stirrer, reflux condenser, dropping funnel and thermometer was charged with 55.3 g (0.3 mol) of cyanuric chloride and 300 g of toluene, which were stirred while heating to an internal temperature of 50° C. To the flask a mixture of 179.3 g (1.4 mol) of γ-aminopropyltrimethoxysilane (KBM-903, Shin-Etsu Chemical Co., Ltd.) and 51.1 g (0.7 mol) of n-butylamine was added dropwise. The reaction was exothermic and the internal temperature rose to 80° C. Stirring was continued for 8 hours while heating to an internal temperature of 110° C. After the reaction, the temperature was adjusted to 80° C. To the flask 81 g (1.3 mol) of ethylenediamine was added dropwise for neutralization over 4 hours. The reaction solution separated into two layers. The upper layer was taken out, from which the solvent and unreacted substances were distilled off under vacuum. The reaction product was left as a pale yellow liquid having a viscosity of 1,450 mm²/s, a specific gravity of 1.12 and a refractive index of 1.454. On NMR spectroscopy, the reaction product was identified to be a compound of the following chemical structural formula (7) having alkoxysilyl and butyl radicals in a ratio of 2:1. $^1$H-NMR spectroscopy data of the compound are shown below.

$^1$H-NMR (300 MHz, CDCl$_3$, δ (ppm)): 0.63 (t, 4H), 0.83 (t, 3H), 1.60-1.69 (m, 8H), 3.22-3.31 (m, 6H), 3.61 (s, 18H), 4.88-5.01 (s, 3H)

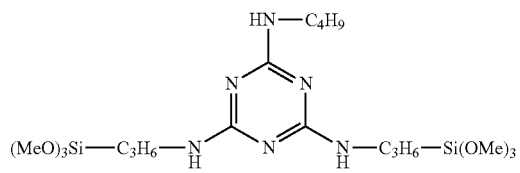

(7)

Example 5

Preparation of N,N-bis(trimethoxysilylpropyl)-N-(polydimethylsiloxypropyl)melamine A 1-L separable flask equipped with a stirrer, reflux condenser, dropping funnel and thermometer was charged with 55.3 g (0.3 mol) of cyanuric chloride and 300 g of toluene, which were stirred while heating to an internal temperature of 50° C. To the flask a mixture of 179.3 g (1.4 mol) of γ-aminopropyltrimethoxysilane (KBM-903, Shin-Etsu Chemical Co., Ltd.) and 135 g (0.3 mol as amino) of a primary amino-terminated polydimethylsiloxane (KF-8010, Shin-Etsu Chemical Co., Ltd.) was added dropwise. The reaction was exothermic and the internal temperature rose to 80° C. Stirring was continued for 8 hours while heating to an internal temperature of 110° C. After the reaction, the temperature was adjusted to 80° C. To the flask 81 g (1.3 mol) of ethylenediamine was added dropwise for neutralization over 4 hours. The reaction solution separated into two layers. The upper layer was taken out, from which the solvent and unreacted substances were distilled off under vacuum. The reaction product was left as a pale yellow liquid having a viscosity of 1,930 mm$^2$/s, a specific gravity of 1.05 and a refractive index of 1.433. On NMR spectroscopy, the reaction product was identified to be a compound having functional radicals, alkoxysilyl and polydimethylsiloxane radicals in an average ratio of 2:1. $^1$H-NMR spectroscopy data of the compound are shown below.

$^1$H-NMR (300 MHz, CDCl$_3$, δ (ppm)): 0.02-0.11 (m, 53H), 0.61-0.64 (m, 4H), 1.63-1.68 (m, 6H), 3.20-3.25 (m, 6H), 3.58-3.64 (m, 18H), 4.88-5.01 (s, 3H)

Japanese Patent Application No. 2009-156463 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing an organosilicon compound of formula (1):

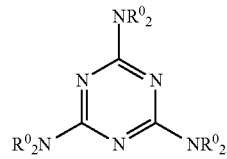

(1)

wherein R$^0$ is independently hydrogen or a substituted or unsubstituted monovalent hydrocarbon radical which may be separated by carbonyl carbon or a heteroatom selected from the group consisting of oxygen, sulfur and nitrogen, and at least one of R$^0$ is the following structure (A):

(A)

wherein the broken line designates a valence bond, X is a substituted or unsubstituted divalent hydrocarbon radical which may be separated by carbonyl carbon or a heteroatom selected from the group consisting of oxygen, sulfur, and nitrogen, the divalent hydrocarbon radical bonding to the nitrogen atom via a carbon atom at one end and bonding to the silicon atom via a carbon atom at the other end, R$^1$ is independently hydrogen or a substituted or unsubstituted C$_1$-C$_4$ alkyl radical, R$^2$ is independently a substituted or unsubstituted C$_1$-C$_4$ alkyl radical, and n is an integer of 1 to 3, said method comprising reacting cyanuric chloride with a primary and/or secondary amine compound, said primary and/or secondary amine compound comprising either an organosilicon compound having the general formula (3):

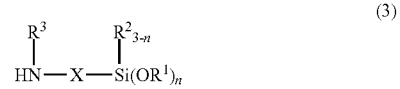

(3)

wherein X is a substituted or unsubstituted divalent hydrocarbon radical which may be separated by carbonyl carbon or a heteroatom selected from the group consisting of oxygen, sulfur, and nitrogen, the divalent hydrocarbon radical bonding to the nitrogen atom via a carbon atom at one end and bonding to the silicon atom via a carbon atom at the other end, R$^1$ is independently hydrogen or a substituted or unsubstituted C$_1$-C$_4$ alkyl radical, R$^2$ is independently a substituted or unsubstituted C$_1$-C$_4$ alkyl radical, R$^3$ is independently hydrogen or a substituted or unsubstituted monovalent hydrocarbon radical which may be separated by carbonyl carbon or a heteroatom selected from the group consisting of oxygen, sulfur, and nitrogen, and n is an integer of 1 to 3, or the organosilicon compound of formula (3) together with another reactant having a primary and/or secondary amino radical, and neutralizing with ethylenediamine.

2. The method of claim 1, wherein the reaction uses at least 4 moles of the organosilicon compound having formula (3) per mole of cyanuric chloride and occurs at a temperature of 25 to 150° C.

3. The method of claim 1, wherein said primary and/or secondary amine compound is the organosilicon compound of the formula (3), and wherein an organosilicon compound of formula (2) is obtained:

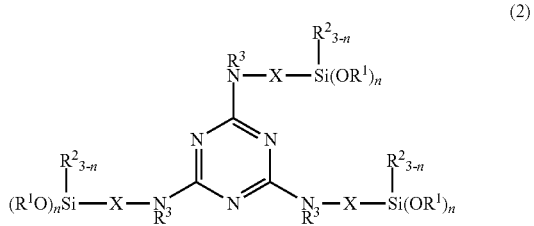

(2)

wherein X is a substituted or unsubstituted divalent hydrocarbon radical which may be separated by carbonyl carbon or a heteroatom selected from the group consisting of oxygen, sulfur, and nitrogen, the divalent hydrocarbon radical bonding to the nitrogen atom via a carbon atom at one end and bonding to the silicon atom via a carbon atom at the other end, $R^1$ is independently hydrogen or a substituted or unsubstituted $C_1$-$C_4$ alkyl radical, $R^2$ is independently a substituted or unsubstituted $C_1$-$C_4$ alkyl radical, $R^3$ is independently hydrogen or a substituted or unsubstituted monovalent hydrocarbon radical which may be separated by carbonyl carbon or a heteroatom selected from the group consisting of oxygen, sulfur, and nitrogen, and n is an integer of 1 to 3.

4. The method of claim 1, wherein the divalent hydrocarbon radical X is methylene, ethylene, propylene, 1-methylpropylene, 2-methylpropylene, 3-methylpropylene, or butylene.

* * * * *